US00PP19716P2

(12) United States Plant Patent
Dekker

(10) Patent No.: US PP19,716 P2
(45) Date of Patent: Feb. 17, 2009

(54) ***CHRYSANTHEMUM* PLANT NAMED 'DEKSNOWFLAKE'**

(50) Latin Name: *Chrysanthemum×morifolium*
Varietal Denomination: Deksnowflake

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/074,410

(22) Filed: Mar. 3, 2008

(51) Int. Cl.
*A01H 5/00* (2006.01)

(52) U.S. Cl. ..... Plt./294
(58) Field of Classification Search ..... Plt./294
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Deksnowflake', characterized by its semi-double-type inflorescences with oval to obovate-shaped, white-colored ray florets and green-colored disc florets; strong and upright flowering stems; freely flowering habit; early and uniform flowering response; and good postproduction longevity.

1 Drawing Sheet

Botanical designation: *Chrysanthemum×morifolium.*
Cultivar denomination: 'DEKSNOWFLAKE'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Deksnowflake'.

The new *Chrysanthemum* is a product of a planned breeding program conducted by the Inventor in Hensbroek, The Netherlands. The objective of the breeding program is to create new freely flowering semi-double-type *Chrysanthemum* cultivars with unique ray floret coloration and excellent postproduction longevity.

The new *Chrysanthemum* originated from a cross-pollination made by the Inventor in Hensbroek, The Netherlands on Nov. 8, 2004 of a proprietary selection of *Chrysanthemum×morifolium* identified as code number 41414, not patented, as the female, or seed, parent with a proprietary selection of *Chrysanthemum ×morifolium* identified as code number 02.6450.05, not patented. The cultivar Deksnowflake was discovered and selected by the Inventor as a flowering plant from within the progeny of the stated cross-pollination in a controlled environment in Hensbroek, The Netherlands on Apr. 12, 2005.

Asexual reproduction of the new *Chrysanthemum* by terminal cuttings in a controlled environment in a greenhouse in Hensbroek, The Netherlands since May 1, 2005, has shown that the unique features of this new *Chrysanthemum* are stable and reproduced true to type in successive generations.

SUMMARY OF THE INVENTION

Plants of the cultivar Deksnowflake have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deksnowflake'. These characteristics in combination distinguish 'Deksnowflake' as a new and distinct cultivar of *Chrysanthemum:*

1. Semi-double-type inflorescences with oval to obovate-shaped, white-colored ray florets and green-colored disc florets.
2. Strong and upright flowering stems.
3. Freely flowering habit.
4. Early and uniform flowering response; plants flower about 48 days after the start of photoinductive treatments.
5. Good postproduction longevity; plants maintain good substance for about three weeks in an interior environment.

Plants of the new *Chrysanthemum* differ from plants of the female parent selection in the following characteristics:

1. Plants of the new *Chrysanthemum* the have smaller leaves than plants of the female parent selection.
2. Plants of the new *Chrysanthemum* have larger inflorescences than plants of the female parent selection.
3. Plants of the new *Chrysanthemum* flower earlier than plants of the female parent selection.

Plants of the new *Chrysanthemum* differ from plants of the male parent selection in the following characteristics:

1. Plants of the new *Chrysanthemum* are not as vigorous as plants of the male parent selection.
2. Plants of the new *Chrysanthemum* flower earlier than plants of the male parent selection.
3. Plants of the new *Chrysanthemum* are more freely flowering than plants of the male parent selection.

Plants of the new *Chrysanthemum* can be compared to plants of the *Chrysanthemum* cultivar Noa, disclosed in U.S. Plant Pat. No. 17,855. In side-by-side comparisons conducted in Hensbroek, The Netherlands, plants of the new

*Chrysanthemum* differed from plants of the cultivar Noa in the following characteristics:

1. Plants of the new *Chrysanthemum* were not as vigorous as plants of the cultivar Noa.
2. Plants of the new *Chrysanthemum* were more freely branching than plants of the cultivar Noa.
3. Plants of the new *Chrysanthemum* had more ray florets per inflorescence than plants of the cultivar Noa.

BRIEF DESCRIPTION OF THE PHOTOGRAPHS

The accompanying colored photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Deksnowflake' grown as a spray type.

The photograph at the bottom of the sheet is a close-up view of typical inflorescences of 'Deksnowflake'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the autumn in Hensbroek, The Netherlands, under commercial practice in a glass-covered greenhouse. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were about nine weeks from planting when the photographs and the description were taken.

Botanical classification:

Chrysanthemum×morifolium cultivar Deksnowflake.

Parentage:

*Female, or seed, parent.*—Proprietary selection of *Chrysanthemum×morifolium* identified as code number 41414, not patented.

*Male, or pollen, parent.*—Proprietary selection of *Chrysanthemum×morifolium* identified as code number 02.6450.05, not patented.

Propagation:

*Type.*—Terminal vegetative cuttings.

*Time to initiate roots.*—About six to seven days at 20° C.

*Time to produce a rooted young plant.*—About 13 to 15 days at 20° C.

*Root description.*—Fine, fibrous; light brown in color.

*Rooting habit.*—Freely branching, moderately dense.

Plant description:

*Appearance/growth habit.*—Herbaceous semi-double-type cut flower that is typically grown as a spray-type. Moderately vigorous growth habit.

*Flowering stem description.*—Aspect: Erect. Length: About 75 cm. Spray diameter: About 15 cm to 20 cm. Diameter: About 6 mm to 8 mm. Number of lateral branches: About 12 to 14. Internode length: About 1.5 cm to 2 cm. Texture: Pubescent; longitudinally ridged. Color: Close to 146B.

*Foliage description.*—Arrangement: Alternate; simple. Length: About 6.5 cm to 12 cm. Width: About 4.5 cm to 7 cm. Apex: Cuspidate. Base: Attenuate. Margin: Palmately lobed; sinuses parallel to convergent. Texture, upper and lower surfaces: Pubescent, rough; veins prominent on lower surface. Venation pattern: Pinnate, reticulate. Color: Developing foliage, upper surface: Close to 144A. Developing foliage, lower surface: Lighter than 138B. Fully expanded foliage, upper surface: Close to 147A; venation, close to 148B. Fully expanded foliage, lower surface: Close to 147B; venation, 147B. Petiole: Length: About 1 cm to 2.5 cm. Diameter: About 2.5 mm to 3.5 mm. Texture, upper and lower surfaces: Slightly rough. Color, upper and lower surfaces: Close to 146B.

Inflorescence description:

*Appearance.*—Semi-double-type inflorescence form with oblong-shaped ray florets. Inflorescences borne on terminals, arising from leaf axils. Ray and disc florets develop acropetally on a capitulum. Inflorescences slightly fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about 48 days later when grown as a spray-type.

*Postproduction longevity.*—In an interior environment, inflorescences and foliage will maintain good color and substance for about three weeks.

*Quantity of inflorescences.*—When grown as a spray type, freely flowering habit, about 15 to 20 inflorescences per flowering stem develop.

*Inflorescence size.*—Diameter: About 6 cm. Depth (height): About 1.5 cm. Disc diameter: About 1.5 cm. Receptacle height: About 3 mm. Receptacle diameter: About 6 mm. Receptacle color: Close to 145B.

*Inflorescence buds.*—Shape: Oblate. Height: About 5 mm. Diameter: About 8 mm. Color: Close to 137C to 137D.

*Ray florets.*—Length: About 3 cm to 3.5 cm. Width: About 1.3 cm to 1.5 cm. Shape: Oval to obovate. Apex: Obtuse or emarginate. Base: Attenuate. Margin: Entire. Angle: Initially upright to close to perpendicular to the peduncle. Texture, upper and lower surfaces: Smooth, glabrous; satiny. Number per inflorescence: About 30 arranged in two whorls. Color: When opening, upper and lower surfaces: Close to 155D. Fully opened, upper and lower surfaces: Close to 155D.

*Disc florets.*—Shape: Fused tubular, elongated. Apex: Dentate. Length: About 4 mm to 6 mm. Diameter: About 0.5 mm to 1 mm. Number per inflorescence: About 225. Color: Immature: Apex: Close to 144A to 144B. Mid-section: Close to 154B. Base: Close to 145D. Mature: Apex: Close to 5A. Mid-section: Close to 145C. Base: Close to 145D.

*Involucral bracts.*—Length: About 9 mm to 11 mm. Width: About 6 mm to 8 mm. Shape: Ovate. Apex: Rounded, obtuse. Base: Truncate to obtuse. Margin:

Entire. Texture, upper surface: Smooth, glabrous. Texture, lower surface: Pubescent, slightly rough. Number per inflorescence: About 25 arranged in two or three whorls. Color, upper surface: Close to 137C. Color, lower surface: Close to 137B to 137C.

*Peduncles.*—Length, fourth peduncle: About 8 cm to 9 cm. Length, seventh peduncle: About 10 cm. Diameter: About 2 mm to 3 mm. Angle: About 30° from vertical. Strength: Moderately strong to strong. Texture: Pubescent; longitudinally ridged. Color: Close to 146A.

*Reproductive organs.*—Androecium: Not observed. Gynoecium: Present on both ray and disc florets. Style length: About 5 mm. Style color: Close to 4D.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dek-snowflake' as illustrated and described.

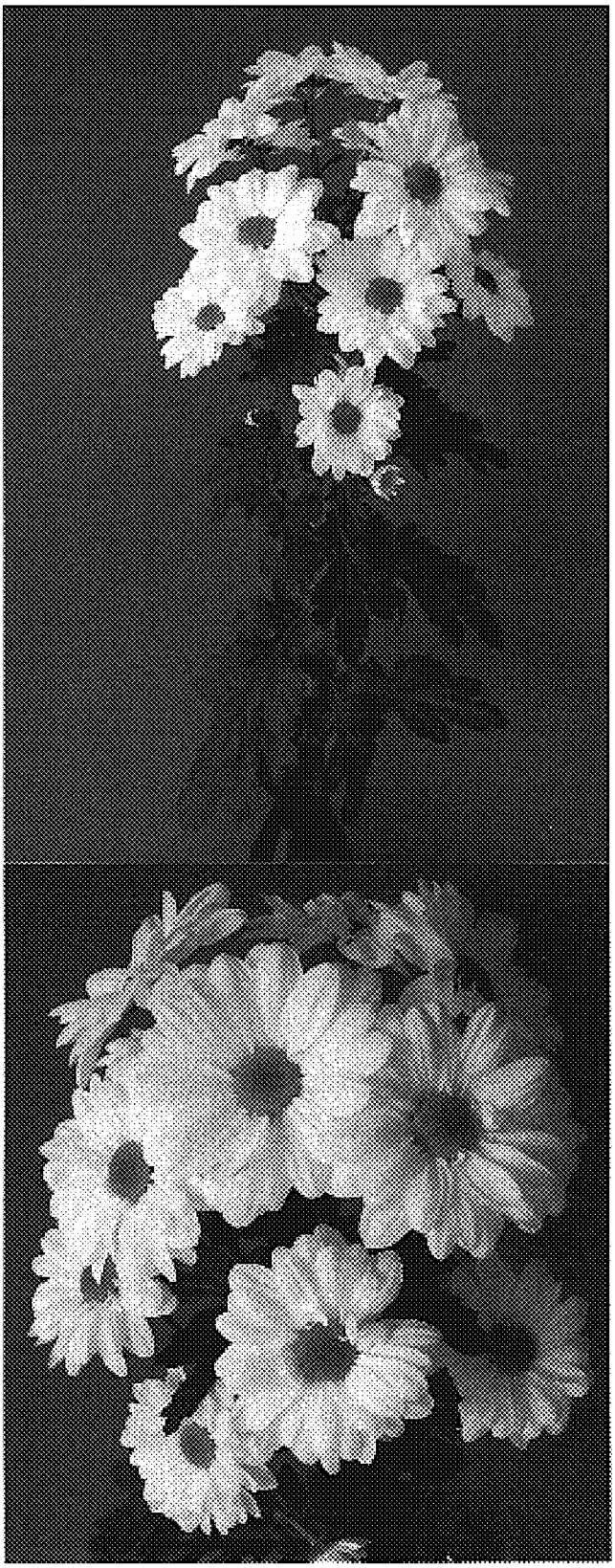

* * * * *